US010326973B2

(12) United States Patent
Okabe et al.

(10) Patent No.: US 10,326,973 B2
(45) Date of Patent: Jun. 18, 2019

(54) TIME SERIES DATA DISPLAY CONTROL DEVICE, METHOD FOR OPERATING THE SAME, PROGRAM, AND SYSTEM

(71) Applicant: FUJIFILM Corporation, Tokyo (JP)

(72) Inventors: Yuuki Okabe, Tokyo (JP); Yasuyo Nenoki, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 101 days.

(21) Appl. No.: 15/498,411

(22) Filed: Apr. 26, 2017

(65) Prior Publication Data

US 2017/0230632 A1 Aug. 10, 2017

Related U.S. Application Data

(63) Continuation of application No. PCT/JP2015/076562, filed on Sep. 17, 2015.

(30) Foreign Application Priority Data

Nov. 21, 2014 (JP) ................. 2014-237156

(51) Int. Cl.
*G06T 11/20* (2006.01)
*H04N 13/106* (2018.01)
(Continued)

(52) U.S. Cl.
CPC ........... *H04N 13/106* (2018.05); *A61B 5/743* (2013.01); *A61B 5/7435* (2013.01);
(Continued)

(58) Field of Classification Search
CPC ............... H04N 13/359; H04N 13/356; H04N 21/8146; G06F 3/04842; G06T 2200/04
See application file for complete search history.

(56) References Cited

U.S. PATENT DOCUMENTS 8,502,821 B2 * 8/2013 Louise ............... G01R 13/0236
345/419
2005/0234670 A1 * 10/2005 Hagen ................. G01R 13/206
702/85
(Continued)

FOREIGN PATENT DOCUMENTS

JP H06-243264 9/1994
JP 2012148079 8/2012

OTHER PUBLICATIONS

"Written Opinion of the International Searching Authority (Form PCT/ISA/237) of PCT/JP2015/076562", dated Dec. 22, 2015, with English translation thereof, pp. 1-9.
(Continued)

*Primary Examiner* — Martin Mushambo
(74) *Attorney, Agent, or Firm* — JCIPRNET

(57) ABSTRACT

A main display region 41 in which medical care data on a plurality of items is displayed is provided on the display screen 15. The main display region 41 may be displayed in two display modes of a two-dimensional display mode and a three-dimensional display mode in which a two-dimensional plane on which time series data is displayed is three-dimensionally displayed using the laws of perspective. In the three-dimensional display mode, a summary window for displaying a summary of data content of the plurality of pieces of time series data at an arbitrary point in time designated on a time axis.

19 Claims, 11 Drawing Sheets

(51) Int. Cl.
  *A61B 5/00*      (2006.01)
  *G09G 5/00*      (2006.01)
  *G06F 3/0481*    (2013.01)
  *G09G 3/00*          (2006.01)

(52) U.S. Cl.
  CPC ........... *G06F 3/04815* (2013.01); *G09G 5/00* (2013.01); *G09G 3/003* (2013.01); *G09G 2340/04* (2013.01); *G09G 2340/14* (2013.01); *G09G 2380/08* (2013.01)

(56) References Cited

U.S. PATENT DOCUMENTS

| | | | | |
|---|---|---|---|---|
| 2005/0286679 | A1* | 12/2005 | Sakaguchi | A61B 6/032 378/8 |
| 2006/0012596 | A1* | 1/2006 | Fukuya | G06T 19/00 345/419 |
| 2011/0074416 | A1* | 3/2011 | Yamashita | A61B 5/055 324/309 |
| 2012/0169729 | A1* | 7/2012 | Yamaji | H04N 13/361 345/419 |
| 2012/0182301 | A1 | 7/2012 | Wenholz et al. | |
| 2012/0314024 | A1* | 12/2012 | Tsang | G09G 3/003 348/43 |
| 2013/0093781 | A1* | 4/2013 | Suzuki | A61B 6/461 345/581 |
| 2013/0106996 | A1* | 5/2013 | Tsai | G09G 5/005 348/43 |
| 2013/0181968 | A1* | 7/2013 | Uemura | G02B 27/2214 345/212 |
| 2015/0201187 | A1* | 7/2015 | Ryo | G09G 5/00 348/51 |
| 2015/0257739 | A1* | 9/2015 | Yao | A61B 8/06 600/431 |
| 2015/0260815 | A1* | 9/2015 | Nishihara | G01R 33/4836 324/309 |
| 2016/0357439 | A1* | 12/2016 | Uehara | G06F 3/0604 |

OTHER PUBLICATIONS

"International Search Report (Form PCT/ISA/210) of PCT/JP2015/076562", dated Dec. 22, 2015, with English translation thereof, pp. 1-4.

\* cited by examiner

TIME SERIES DATA DISPLAY CONTROL DEVICE, METHOD FOR OPERATING THE SAME, PROGRAM, AND SYSTEM

CROSS-REFERENCE TO RELATED APPLICATIONS

This application is a Continuation of PCT International Application No. PCT/JP2015/076562 filed on Sep. 17, 2015, which claims priority under 35 U.S.C § 119(a) to Patent Application No. 2014-237156 filed in Japan on Nov. 21, 2014, all of which are hereby expressly incorporated by reference into the present application.

BACKGROUND OF THE INVENTION

1. Field of the Invention

The present invention relates to a time series data display control device, a method for operating the same, a non-transitory computer readable recording medium storing a program, and a system.

2. Description of the Related Art

Devices that display time series data indicating time-dependent changes in data have been used in various fields. For example, JP2012-148079A discloses a device that displays time series data indicating time-dependent changes in data on medical care, such as a blood pressure, a body temperature or a heart rate of a patient, on a display screen in a medical field (JP2012-148079A). The time series data is two-dimensionally displayed, for example, on a two-dimensional plane formed by a time axis and an array axis orthogonal to the time axis for arraying a plurality of pieces of time series data (FIG. 4). Further, a display device disclosed in JP1994-243264A (JP-H6-243264A) shows a technique that three-dimensionally displays time series data. More specifically, a longitudinal direction of a virtual cylinder is set as a time axis, and a plurality of pieces of time series data are allocated to a circumferential surface thereof. Further, the plurality of pieces of time series data are displayed in such a form that observation is performed with a point of view being inside the virtual cylinder and with eyes being directed along the longitudinal direction (<0014>to <0017>, and FIG. 5).

In JP1994-243264A (JP-H6-243264A), the virtual cylinder is set as an allocation region of the plurality of pieces of time series data for the purpose of reducing overlap of the plurality of pieces of time series data. That is, in a case where the plurality of pieces of time series data are two-dimensionally displayed, an array axis direction orthogonal to the time axis and a direction in which values of time series data vary overlap each other. Thus, if the data fluctuation is large, the plurality of pieces of time series data overlap each other, which makes it hard to see the data. In order to handle this problem, in JP1994-243264A (JP-H6-243264A), by setting the virtual cylinder, it is possible to reduce the overlap of the plurality of pieces of time series data by enlarging the allocation region of the plurality of pieces of time series data in comparison with the two-dimensional plane.

In the three-dimensional display disclosed in FIG. 5 of JP1994-243264A (JP-H6-243264A), the plurality of pieces of time series data allocated to the circumferential surface of the virtual cylinder are radially displayed from the center of the cylinder. Further, in the above-described three-dimensional display, using a screen scroll operation, the time axis can be scrolled, and enlargement display or reduction display of the time series data can also be performed.

SUMMARY OF THE INVENTION

In the two-dimensional display technique disclosed in JP2012-148079A, it is possible to easily recognize detailed data changes, whereas in the three-dimensional display technique disclosed in JP1994-243264A (JP-H6-243264A), it is possible to prevent overlap of a plurality of pieces of time series data, to thereby provide convenience in a case where time series data of a large amount of data items are displayed. For example, time series data on medical care has a large amount of data items to be referred to in diagnosis, and thus, it is necessary to generally recognize the tendency of the respective data items, and contrarily, to pay attention to detailed changes. In order to respond to these demands, the inventors have reviewed a combination of the two-dimensional display technique disclosed in JP2012-148079A and the three-dimensional display technique disclosed in JP1994-243264A (JP-H6-243264A).

However, if the display is performed in the form that the plurality of pieces of time series data are allocated on the circumferential surface of the virtual cylinder as in the three-dimensional display disclosed in JP1994-243264A (JP-H6-243264A), there is a problem in that it is difficult to recognize data content at an arbitrary time on the time axis as compared with the two-dimensional display. Specifically, in the case of the two-dimensional display, since a plurality of pieces of time series data at an arbitrary time point are arranged on the same straight line, data content of the respective time series data, for example, data content such as numerical values of blood pressures or numerical values of body temperatures at an arbitrary time point is easily recognized at a glance. On the other hand, in the three-dimensional display, since a plurality of pieces of time series data are dispersed and arranged in a circumferential direction of a virtual cylinder, it is difficult to recognize data content of a plurality of pieces of time series data at an arbitrary time point.

In determination of a medical care policy, since the determination is made focusing on a relationship between a plurality of data items of the medical care data, it is highly necessary to easily recognize content of the plurality of data items at an arbitrary time point. JP2012-148079A and JP1994-243264A (JP-H6-243264A) neither disclose nor suggest any such issues or solutions.

An object of the invention is to provide a time series data display control device, a method for operating the same, a non-transitory computer readable recording medium storing a program, and a system capable of simply recognizing, when performing both a two-dimensional display and a three-dimensional display of time series data, data content of a plurality of pieces of time series data at an arbitrary time point even in the three-dimensional display.

In order to solve the above problems, according to an aspect of the invention, there is provided a time series data display control device including a screen data generating unit and a screen display control unit. The screen data generating unit generates a time series data display screen on which a plurality of pieces of time series data are displayed. The screen display control unit performs switching between display modes of the time series data display screen, in which the display modes include two display modes of a two-dimensional display mode in which the time series data is displayed on a two-dimensional plane formed by two axes of a time axis of the plurality of pieces of time series data and a data array axis orthogonal to the time axis, on which the plurality of pieces of time series data are arrayed, and a three-dimensional display mode in which the two-dimensional plane is three-dimensionally displayed using the laws of perspective by which a plurality of straight lines parallel to the time axis in the two-dimensional display mode are drawn to be converged toward the past on the time axis. Further, the screen display control unit is able to display a summary window for displaying a summary of data content of the plurality of pieces of time series data at a designated point in time on the time axis, in the three-dimensional display mode.

It is preferable that the summary window is provided in the form of a two-dimensional plane developed in a direction orthogonal to the time axis at an arbitrary point in time designated on the time axis.

It is preferable that in the three-dimensional display mode, a virtual rectangular box having a longitudinal direction that coincides with the time axis and displayed by the laws of perspective is set in the time series data display screen, and the plurality of pieces of time series data are displayed on at least a part of an inner circumferential surface of the rectangular box.

It is preferable that the inner circumferential surface is formed by three surfaces of a bottom surface, and both side surfaces rising from both ends of the bottom surface.

In the three-dimensional display mode, an item name display region indicating respective item names of the plurality of pieces of time series data may be two-dimensionally displayed.

It is preferable that the item name display region is disposed at the end of the current direction on the time axis, on the time series data display screen.

It is preferable that on the time series data display screen, a period during which the time series data does not exist is compressed in the time axis direction to be displayed.

It is preferable that the time series data is medical care data relating to a medical care of a patient.

According to another aspect of the invention, there is provided a method for operating a time series data display control device, including a screen data generating step and a screen display control step. The screen data generating step is a step of generating a time series data display screen on which a plurality of pieces of time series data are displayed. The screen display control step is a step of performing switching between display modes of the time series data display screen, in which the display modes include two display modes of a two-dimensional display mode in which the time series data is displayed on a two-dimensional plane formed by two axes of a time axis of the plurality of pieces of time series data and a data array axis orthogonal to the time axis, on which the plurality of pieces of time series data are arrayed, and a three-dimensional display mode in which the two-dimensional plane on which the time series data is displayed is three-dimensionally displayed using the laws of perspective by which a plurality of straight lines parallel to the time axis in the two-dimensional display mode are drawn to be converged toward the past on the time axis. Further, in the screen display control step, a summary window for displaying a summary of data content of the plurality of pieces of time series data at a designated point in time on the time axis is able to be displayed in the three-dimensional display mode.

According to still another aspect of the invention, there is provided a time series data display control program that causes a computer to function as a time series data display control device, including a screen data generating step and a screen display control step. The screen data generating step is a step of generating a time series data display screen on which a plurality of pieces of time series data are displayed. The screen display control step is a step of performing switching between display modes of the time series data display screen, in which the display modes include two display modes of a two-dimensional display mode in which the time series data is displayed on a two-dimensional plane formed by two axes of a time axis of the plurality of pieces of time series data and a data array axis orthogonal to the time axis, on which the plurality of pieces of time series data are arrayed, and a three-dimensional display mode in which the two-dimensional plane on which the time series data is displayed is three-dimensionally displayed using the laws of perspective by which a plurality of straight lines parallel to the time axis in the two-dimensional display mode are drawn to be converged toward the past on the time axis. Further, in the screen display control step, a summary window for displaying a summary of data content of the plurality of pieces of time series data at a designated point in time on the time axis is able to be displayed in the three-dimensional display mode.

According to still another aspect of the invention, there is provided a time series data display control system including a screen data generating unit and a screen display control unit. The screen data generating unit generates a time series data display screen on which a plurality of pieces of time series data are displayed. The screen display control unit performs switching between display modes of the time series data display screen, in which the display modes include two display modes of a two-dimensional display mode in which the time series data is displayed on a two-dimensional plane formed by two axes of a time axis of the plurality of pieces of time series data and a data array axis orthogonal to the time axis, on which the plurality of pieces of time series data are arrayed, and a three-dimensional display mode in which the two-dimensional plane on which the time series data is displayed is three-dimensionally displayed using the laws of perspective by which a plurality of straight lines parallel to the time axis in the two-dimensional display mode are drawn to be converged toward the past on the time axis. Further, the screen display control unit is able to display a summary window for displaying a summary of data content of the plurality of pieces of time series data at a designated point in time on the time axis, in the three-dimensional display mode.

According to the invention, in a case where both a two-dimensional display and a three-dimensional display of time series data are performed, it is possible to easily recognize data content of a plurality of pieces of time series data at an arbitrary point in time even in the three-dimensional display.

BRIEF DESCRIPTION OF THE DRAWINGS

FIG. 4 is a block diagram showing a configuration of a computer used in a medical care support server or the like.

DESCRIPTION OF THE PREFERRED EMBODIMENTS

First Embodiment

Figure 1:
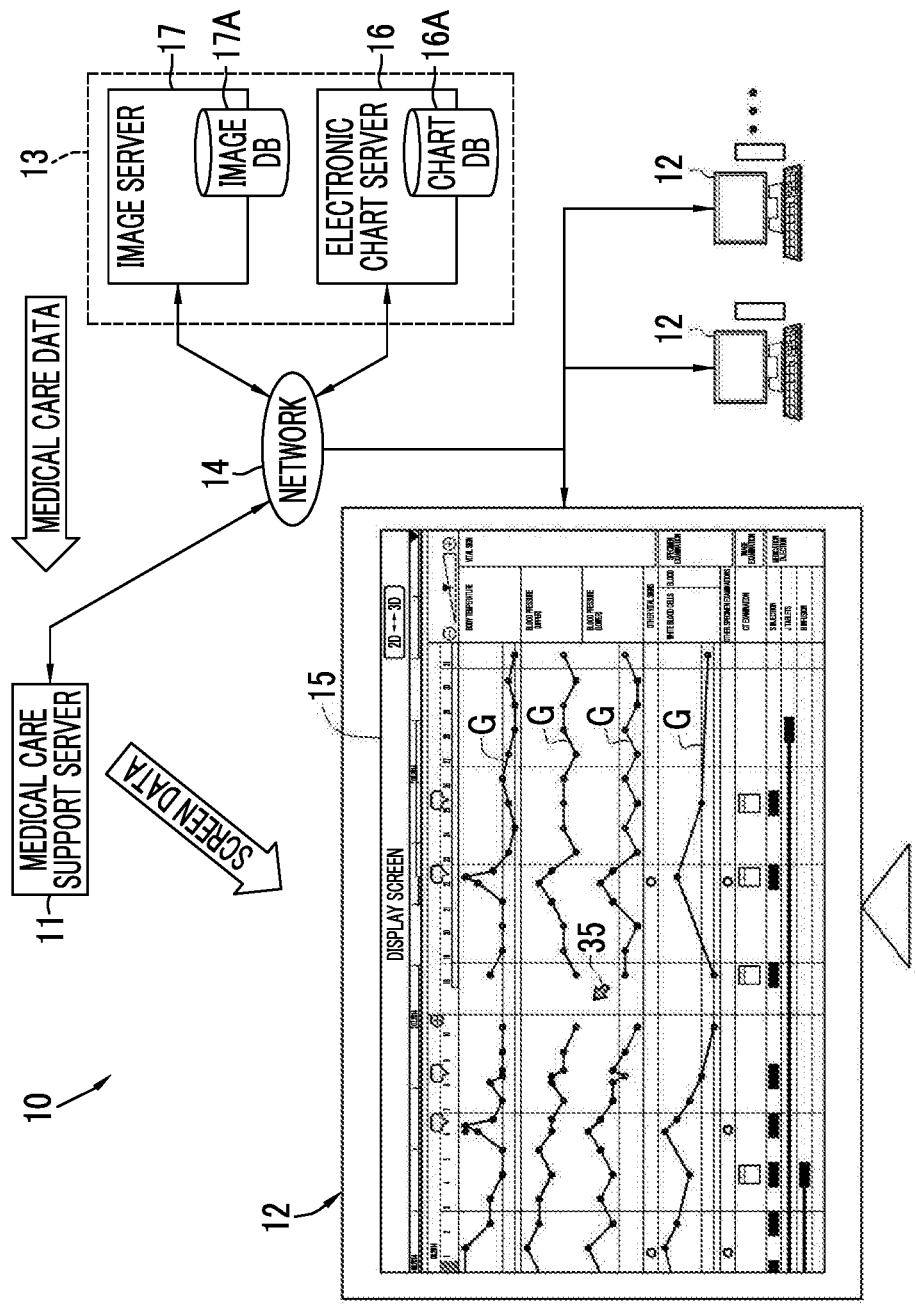
FIG. 1 is a diagram illustrating a medical information system.

A medical information system 10 shown in FIG. 1 is a computer system used for managing and using medical information at medical facilities such as hospitals. The medical information system 10 includes a medical care support server 11 which is a first embodiment of a time series data display control device of the invention, a client terminal 12, a server group 13, and a network 14 that connect these devices for communication.

The server group 13 represents servers that store medical care data of a patient. The server group 13 includes an electronic chart server 16, an image server 17, and the like. The network 14 is a local area network (LAN) provided in a hospital, for example.

The client terminal 12 is a terminal provided in each medical department such as internal medicine, surgery, otolaryngology, or ophthalmology, and is operated by a doctor in the medical department, for example. The client terminal 12 has a function of accessing the electronic chart server 16 to input or view an electronic chart. In the electronic chart, medical care data including diagnosis records such as inquiries and diagnosis content, measurement values of medical examination and measured values of vital signs, or treatment records such as treatment or surgery is input. Further, the client terminal 12 has a function of accessing the image server 17 to view examination images such as X-ray images. In this way, the client terminal 12 functions as a viewer terminal for viewing medical care data.

Further, the client terminal 12 accesses the medical care support server 11 to receive distribution of screen data on a time series data display screen (hereinafter, referred to as a display screen) 15 that displays time series data indicating time-dependent changes of medical care data of a patient, and displays the distributed display screen 15. The display screen 15 is able to collectively display examination values or measurement values in medical examination included in an electronic chart and examination images in one screen, unlike a chart display screen exclusive for the electronic chart or an image display screen exclusive for the examination images. On the display screen 15, time series data indicating time-dependent changes of the examination values or the measurement values is displayed in the form of a polygonal line graph G, for example.

The medical care support server 11 receives a distribution request of medical care data including patient designation from the client terminal 12. The medical care support server 11 acquires medical care data of a designated patient from the electronic chart server 16 or the image server 17 on the basis of the distribution request. The medical care support server 11 generates screen data for the display screen 15 on the basis of the acquired medical care data, and distributes the screen data to the client terminal 12 which is a request source. Further, the medical care support server 11 has a function of editing screen data according to the request from the client terminal 12 to perform a screen display control of the display screen 15, and functions as a time series data display control device of the invention.

The electronic chart server 16 includes an electronic chart database (hereinafter, referred to as a chart database (DB)) 16A in which an electronic chart is stored. The image server 17 includes an image DB 17A in which a plurality of examination images are stored, and is a so-called a picture achieving and communication system (PACS) server. The chart DB 16A and the image DB 17A are databases capable of being retrieved using keywords such as patient identification data (ID).

Figure 2:
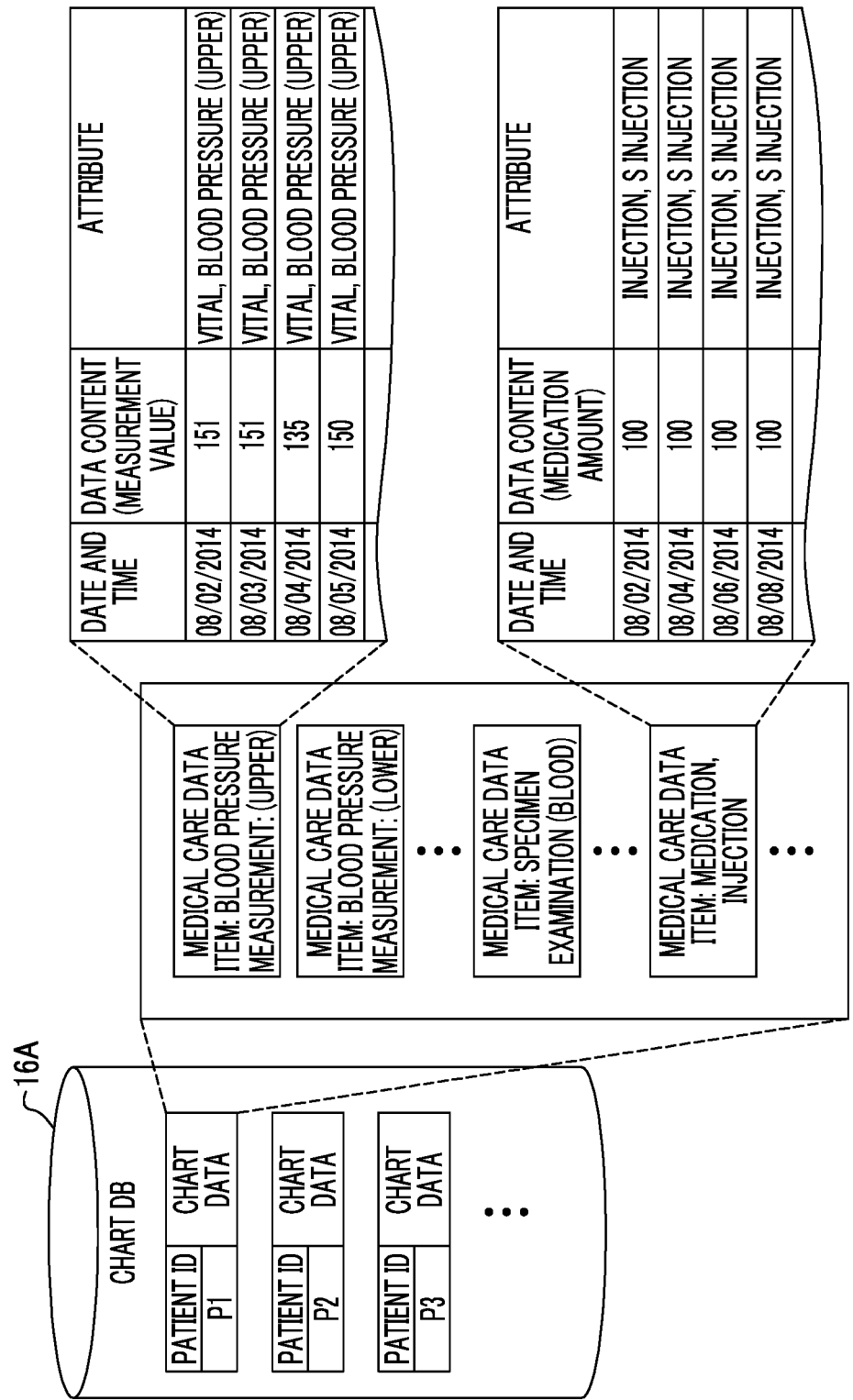
FIG. 2 is a diagram illustrating medical care data recorded in an electronic chart.

As shown in FIG. 2, the chart DB 16A stores chart data in which medical care data of a patient is stored. The chart data is assigned patent ID (P1, P2, . . . ) and is managed in the unit of patients. The chart data includes basic patient information such as a name, a birthday, a gender and a patient ID of a patient, and medical care data of the patient.

The medical care data includes measurement values of vital signs such as a heartbeat, a pulse rate, a blood pressure, and a body temperature of a patient, and examination values of clinical examinations performed for the patient. The clinical examinations include specimen examinations such as blood examination or a biochemical examination, and electroencephalography examinations such as a physiological examination. In addition, the medical care data includes details of medical treatment given to the patient, specifically, content of treatment such as medication, injection, surgery or treatment, content of inquiries. In this way, a plurality of items are included in the medical care data, and in FIG. 2, as the medical care data, items such as measurement values of a blood pressure (upper) and a blood pressure (lower), examination values of a specimen examination (blood examination), or injection dosages of S injection.

A record of one item among the respective items of the medical care data includes information on dates and times such as examination dates or measurement dates, content of acquired data (examination value or measurement value), and attributes thereof. The information on dates and times indicates measurement dates and times if it relates to measurement values, indicates examination dates and times if it relates to examination values, and indicates medication or injection dates and times or medicine prescription date and times if it relates to medication or injection. Since medication may take a period of time until an effect appears, for example, medication (taking medicine) over a predetermined period of time, such as "take a certain dose everyday for 5 days", may be instructed by one-time prescription. In this case, as the medication time and date, the date and time scheduled to be taken is recorded.

The attributes represent information given for sorting of data, and represent information indicating attributes of each item of the medical care data. The attributes may also be used as keywords for retrieval of the medical care data. The attributes include an item name ("blood pressure (upper)" or the like) of the medical care data, a category to which an item belongs ("vital"), and the like, for example. In addition to an item name "injection", a medication name "S" injection liquid, for example, may be given to an item of medication or injection.

Figure 3:
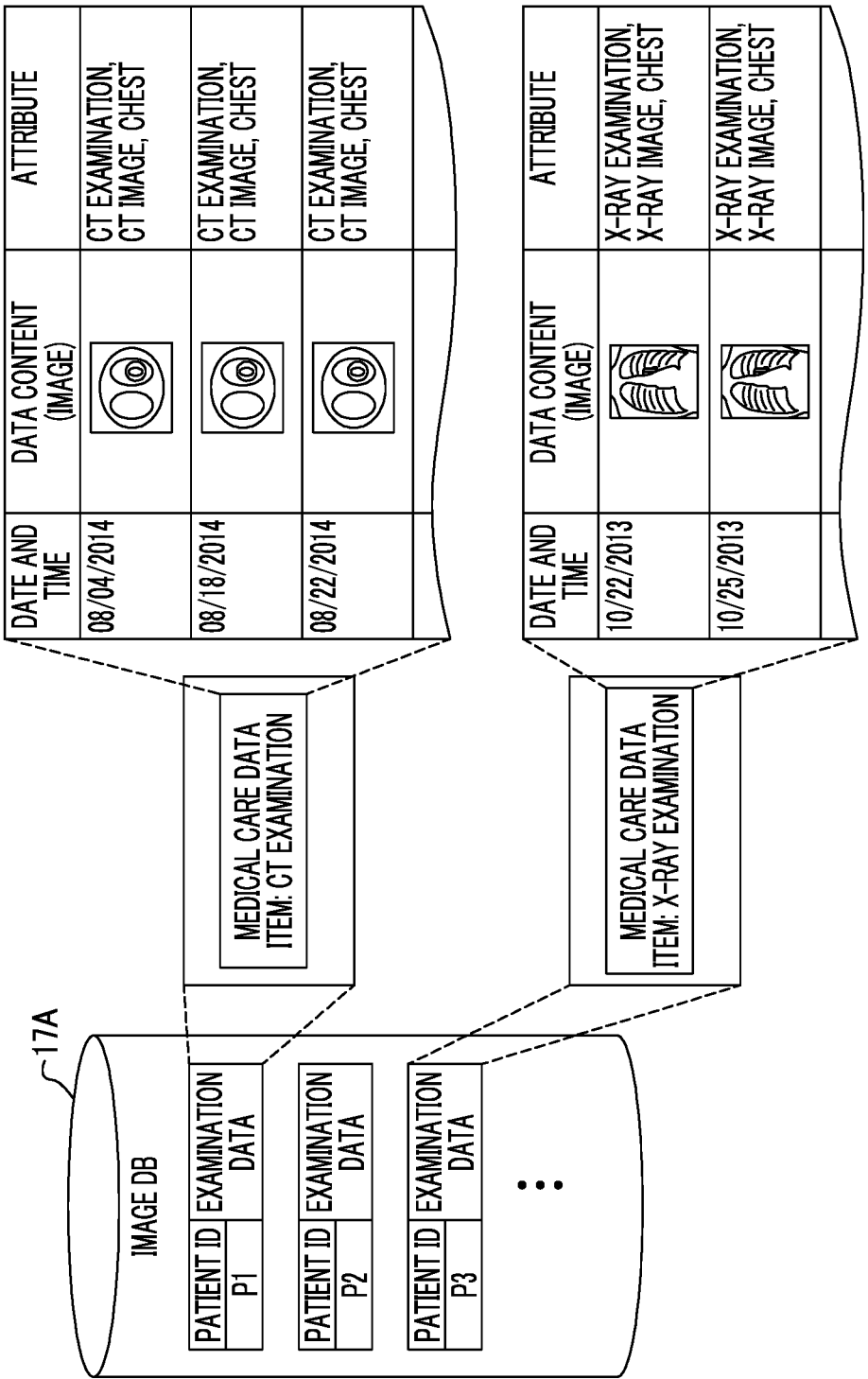
FIG. 3 is a diagram illustrating medical care data recorded in an image server.

As shown in FIG. 3, the image DB 17A stores examination data formed by a plurality of examination images captured in image examination such as X-ray examination or CT examination. A patient ID is given to the examination images, and the examination images may be retrieved using the patient ID. In the image examination, a plurality of examination images may be captured by one examination like a plurality of tomographic images acquired in CT examination. The same examination ID may be given to a plurality of examination images acquired by one examination and may be managed as a one-time examination image. Further, the examination images may be managed every date and time when the image examination is performed.

In addition, content of data of an examination image may include image analysis information obtained by analyzing the examination image, in addition to data on the examination image. The image analysis information may include, for example, information on the size of a lesion in the examination image and the type of the lesion. The image analysis information may be information calculated by image processing, or may be input information of content determined by a doctor based on image observation. The attributes of the examination image include information indicating "X-ray examination", "CT examination" indicating an examination type, "X-ray image" or "CT image" indicating an image type, "chest" or "head" indicating a photographed portion, for example.

The medical care support server 11, the client terminal 12, the electronic chart server 16, and the image server 17 are configured by installing a control program such as an operating system, and an application program such as a client program or a server program in a computer such as a personal computer, a server computer or a workstation, which is a base.

Figure 4:
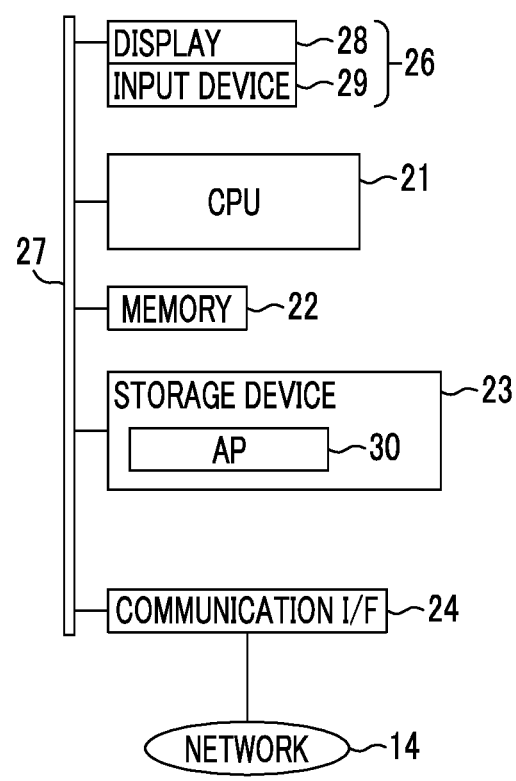

As shown in FIG. 4, computers that configures the respective servers 11, 16, and 17 and the client terminal 12 are the same in basic configurations, and each of the computers includes a central processing unit (CPU) 21, a memory 22, a storage device 23, a communication I/F 24, and an input/output unit 26. These components are connected to each other through a data bus 27. The input/output unit 26 includes a display (display unit) 28, and an input device 29 such as a keyboard or a mouse.

The storage device 23 is, for example, a hard disk drive (HDD), and stores a control program or an application program (hereinafter, referred to as an AP) 30. Further, for example, a disk array in which a plurality of HDDs are continuously provided is provided as the storage device 23 for a DB in a server in which the DB is built, in addition to the HDD that stores the program. The disk array may be provided in a main body of the server, or may be provided separately from the main body of the server and may be connected to the main body of the server through a cable or a network.

The memory 22 is a work memory for execution of processes of the CPU 21, and is configured by a random access memory (RAM). The CPU 21 loads the control program stored in the storage device 23 to the memory 22 and executes processes based on the program, to thereby generally control the respective units of the computer. The communication I/F 24 is a network interface that performs a transmission control with respect to the network 14.

Hereinafter, the CPU 21, the display 28, the storage device 23, and the like which are basic components of the computer shown in FIG. 4 are assigned a subscript sign "A" when being described as components of the client terminal 12, like a CPU 21A, and are assigned a subscript sign "B" when being described as components of the medical care support server 11, like a CPU 21B.

Figure 5:
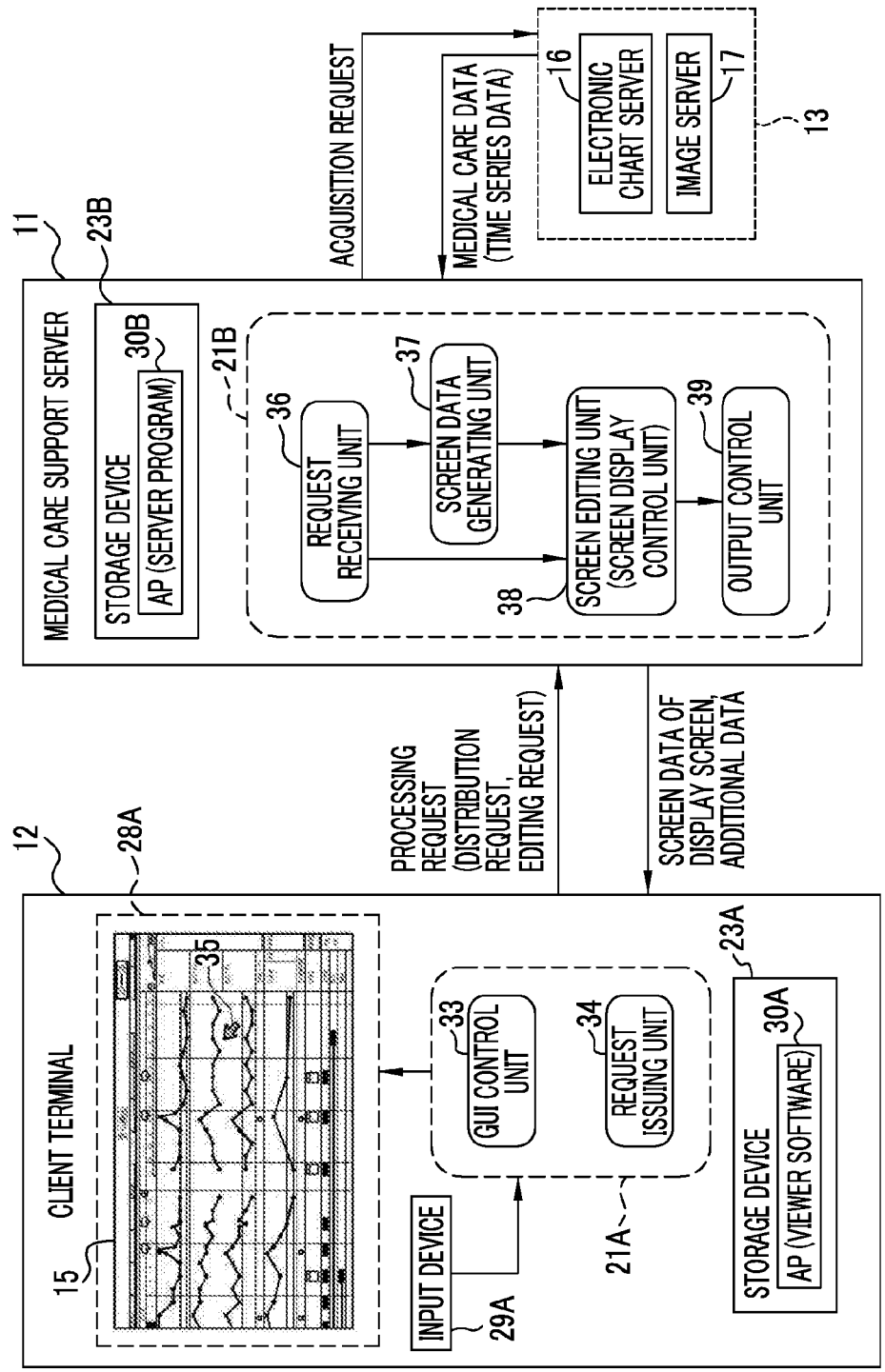
FIG. 5 is a diagram illustrating an overview of functions of a client terminal and a medical care support server.

As shown in FIG. 5, in a storage device 23A of the client terminal 12, a client program such as electronic chart software for viewing or editing of an electronic chart, or viewer software for viewing an examination image or a display screen 15 is installed as an AP 30A. The viewer software may be dedicated software, or may be a general-purpose WEB browser.

In the client terminal 12, if the viewer software is activated, for example, a startup screen including an operating function based on a graphical user interface (GUI) is displayed on a display 28A of the client terminal 12, and the CPU 21A of the client terminal 12 cooperates with the memory 22 or the like to function as a GUI control unit 33 and a request issuing unit 34 that issues various requests to the medical care support server 11. On the startup screen, an operation instruction such as designation of a patient ID or a distribution instruction of medical care data is performed.

The medical care support server 11 distributes screen data that forms the display screen 15. The screen data may be configured by data described in a markup language such as an extensible markup language (XML), for example. The GUI control unit 33 reproduces the display screen 15 on the basis of the received screen data, and displays the display screen 15 on the display 28A. The display screen 15 also functions as an operating screen. The GUI control unit 33 controls the GUI according to an operation instruction input from an input device 29A through the display screen 15, such as a click operation of an operating button using a pointer 35 of a mouse.

The request issuing unit 34 issues a processing request with respect to the medical care support server 11. If designation of a patient ID and a distribution instruction of the display screen 15 are received through the GUI control unit 33, the request issuing unit 34 issues a distribution request of screen data of the display screen 15 as the processing request. The distribution request also includes a distribution request of additional data of medical care data. In a case where the medical care data is time series data obtained over a long period, there is a case where the data over the entire period cannot be delivered at once. In such a case, in response to designation of a display period on the display screen 15, a screen scroll operation for changing the display period, or the like, the request issuing unit 34 requests the medical care support server 11 to deliver undelivered additional data. Further, if an editing request of the display screen 15 is received through the GUI control unit 33, the request issuing unit 34 issues an editing request. The processing request such as an issued distribution request or editing request is transmitted to the medical care support server 11 through the network 14.

A server program for causing a computer to function as the medical care support server 11 is installed in a storage device 23B of the medical care support server 11, as an AP 30B. In this example, the server program functions as a time series data display control program of the invention. If the server program is executed, the CPU 21B of the medical care support server 11 cooperates with the memory 22 or the like to function as a request receiving unit 36, a screen data generating unit 37, a screen editing unit 38, and an output control unit 39.

The request receiving unit 36 receives a processing request from the client terminal 12. If a distribution request of medical care data, the request receiving unit 36 inputs a distribution command based on content of the distribution request to the screen data generating unit 37. The distribution request includes a designated patient ID, and the request receiving unit 36 inputs a command for generating screen data of the display screen 15 relating to medical care data of the designated patient ID to the screen data generating unit 37.

The screen data generating unit 37 issues an acquisition request of the medical care data of the designated patient ID to the server group 13, and acquires the medical care data. A temporal range of the acquired medical care data is an entire range of the medical care data that exists in the server group 13, for example. For example, in a case where one patient repeatedly receives an intermittent ambulatory care or repeatedly enters and leaves a hospital, medical care data intermittently exists. In this case, the entirety of the intermittent medical care data becomes an acquisition target. The screen data generating unit 37 generates screen data of the display screen 15 that displays the acquired medical care data as time series data.

The editing request input to the request receiving unit 36 is input to the screen editing unit 38. The screen editing unit 38 edits screen data of the display screen 15 on the basis of the editing request. The editing request includes a request for switching between a two-dimensional display mode and a three-dimensional display mode with respect to a display mode of the display screen 15 (which will be described later). The screen editing unit 38 functions as a screen display control unit for performing display mode switching on the basis of the display mode switching request. Further, the screen editing unit 38 performs an editing process with respect to the screen data generated by the screen data generating unit 37 as necessary.

The output control unit 39 performs a control for distributing the screen data of the display screen 15 generated by the screen data generating unit 37, additional data with an additional distribution instruction, edited screen data which is edited by the screen editing unit 38, or the like, to the client terminal 12 through the communication I/F 24.

Figure 6:
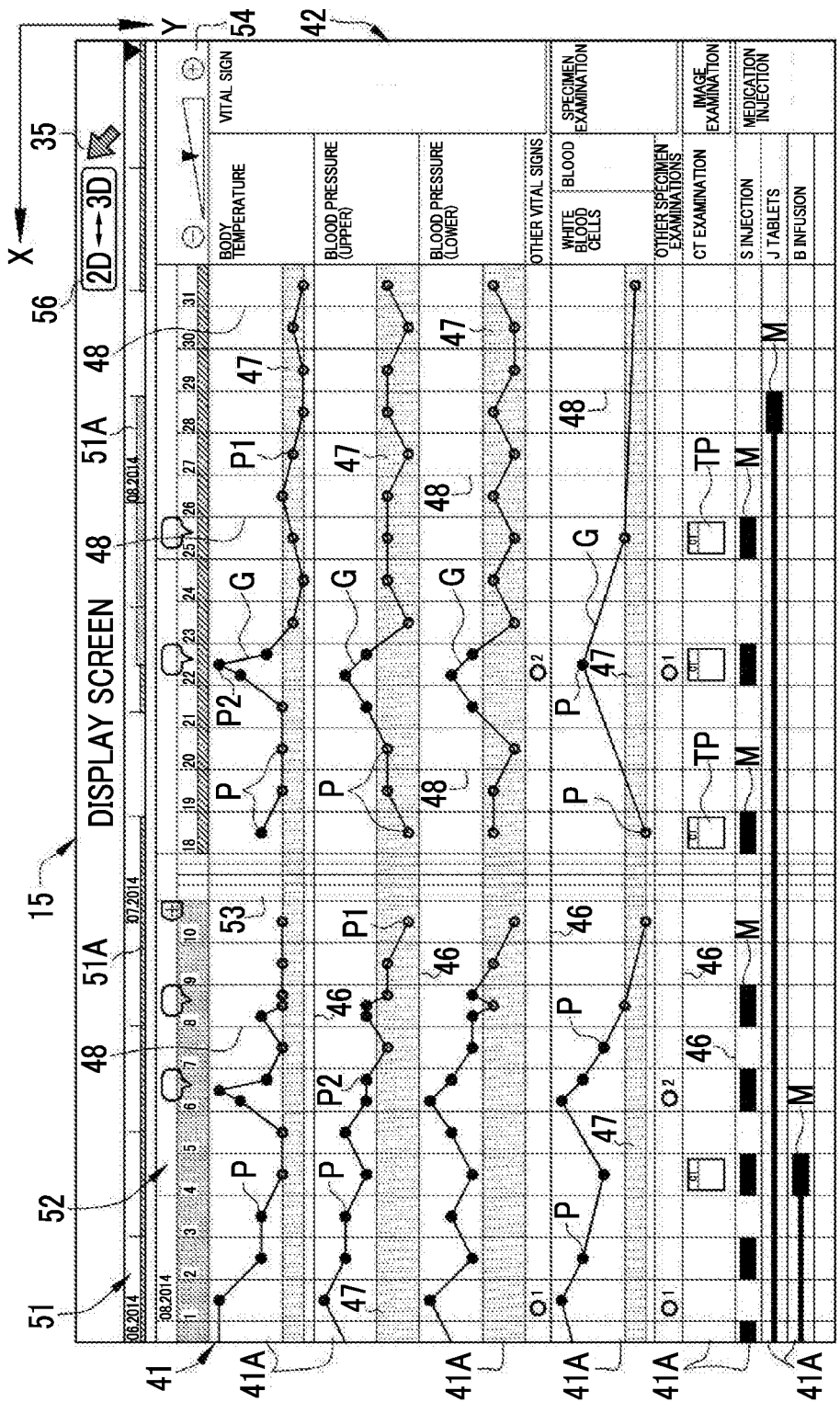
FIG. 6 is a diagram illustrating an example of a display screen in a two-dimensional display mode.

As shown in FIG. 6, the display screen 15 has a main display region 41 and an item name display region 42. In the display screen 15, the transverse axis (X axis) is set as a time axis, and the longitudinal axis (Y axis) is set as a data item array axis, respectively. On the time axis, the left direction represents a past time and the right direction represents a current time. The main display region 41 is a region where a plurality of pieces of medical care data (time series data) are displayed for each data item. The data items of this example include a body temperature, a blood pressure (upper), and a blood pressure (lower) as measurement values of vital signs, white blood cells in blood examination as an examination value of a specimen examination, and examination images in CT examination as examination data in image examination.

The main display region 41 has a plurality of sub regions 41A defined for each data item, and medical care data for each data item is displayed in each sub region 41A. Each sub region 41A is a data display row in which a longitudinal direction extends in the time axis direction and a height indicating each piece of data is shown. The respective sub regions 41A are divided by lateral grid lines 46 extending in the direction of the transverse axis (X axis).

Further, an interval between the lateral grid lines 46 may be adjusted. By adjusting the interval between the lateral grid lines 46, it is possible to adjust the height (the width in the longitudinal axis direction) of each sub region 41A. For example, by designating the lateral grid line 46 using a pointer 35 and performing a drag operation of a mouse, it is possible to change the interval between the lateral grid lines 46. Thus, the height of each sub region 41A can be adjusted.

In each sub region 41A, display forms of medical care data (time series data) vary according to data items. For example, a body temperature, a blood pressure (upper), and a blood pressure (lower) which correspond to data items of vital signs, and white blood cells which corresponds to a data item of a specimen examination are displayed in the form of a polygonal line graph G, respectively. The polygonal line graph G is a graph obtained by connecting input points P where medical care data exists by line segments.

For each examination image, a thumbnail image TP is displayed on an acquisition date of the examination image. The thumbnail image TP is an icon capable of being clicked by a mouse, for example, and an actual image corresponding to the thumbnail image TP is displayed by a click operation.

Further, for S injection liquid, J tablets, and B infusion which correspond to data items of medication and injection, a rectangular mark M indicating that medication is administered at administered date and time is displayed. In the data items of medication and injection, in a case where the administered date and time are continuous like the J tablets and the B infusion, the display is performed in such a form that marks M are displayed on the first date and the last date of the continuously administered period, respectively, and the first date and the last date are connected by a line segment. The respective sub regions 41A are arranged in the longitudinal axis (Y axis), so that the longitudinal axis becomes the data item array axis on the display screen 15.

The height direction of each sub region 41A where the polygonal line graph G is displayed corresponds to a fluctuation direction of data values of the polygonal line graph G. In each sub region 41A, a reference numeral 47 indicated by dot hatching represents a normal range mark indicating a range set as a normal range of data values for each data item. For example, in the case of the body temperature, a range of 36° C. to 37° C. is set as a normal range, and the normal range mark 47 is displayed in the range. The respective normal marks 47 are also displayed with respect to the blood pressure (upper), the blood pressure (lower), and the white blood cells.

Further, in the polygonal line graph G, in a case where a data value is within the normal range, each input point P is displayed by an outline dot which is displayed only with a circular contour line and is not colored inside the contour line, as shown at an input point P1. Further, in a case where a data value is out of the normal range, each input point P is displayed by a solid dot which is colored inside the circular contour line, as shown at an input point P2. In this way, by providing the normal range mark 47, and by selectively using an outline dot and a solid dot as a display form of the input point P depending on whether data value is within the normal range, it is possible to easily recognize whether the data value is normal or not.

In addition, in the main display region 41, vertical grid lines 48 are provided in the longitudinal direction (Y axis) on a daily basis, and the width of a daily column may be specified by an interval between two contiguous vertical grid lines 48. Similar to the lateral grid lines 46, the interval between the vertical grid lines 48 can be adjusted. By adjusting the interval between the vertical grid lines 48, it is possible to increase or decrease the width of the daily column. A method for adjusting the interval between the vertical grid lines 48 may be performed by designating the vertical grid line 48 using the pointer 35 and performing a drag operation of a mouse, similar to the lateral grid line 46.

Further, the screen of the main display region 41 may be scrolled in the transverse direction (X axis direction) and the longitudinal direction (Y axis direction). Through a screen scroll operation in the transverse direction, a display range of medical care data such as the polygonal line graph G displayed in the main display region 41 may be changed. In a case where an ambulatory care period or a hospitalization period of a patient is long, or in a case where a patient repeatedly enters and leaves a hospital, a period during which medical care data exists lasts for a long time. Since the screen size of the display 28A is limited, the entire period of the long-term medical care data cannot be displayed in the main display region 41 at once. In the example shown in FIG. 6, in the entire period during which the medical care data exists, a display range of the main display region 41 corresponding to about one month of August 2014 is displayed. Through the screen scroll operation in the transverse direction, the display range of the main display region 41 may be changed from August 2014 to one month of July or June, for example.

Further, through a screen scroll operation in the longitudinal direction, data items which are not displayed may be displayed. For example, in the example shown in FIG. 6, as the data items of medication and injection, the data items of the S injection, the J tablets, and the B infusion are displayed, but in a case where there is data of additional another medicine that is not displayed, it is possible to display the medicine through the screen scroll operation in the longitudinal direction.

In addition, as described later, the main display region 41 may be displayed in two display modes of a two-dimensional (2D) display mode in which medical care data (time series data) is displayed on a two-dimensional plane formed by two axes of the time axis (transverse axis) and the data array axis (longitudinal axis), as shown in FIG. 6, and a three-dimensional (3D) display mode (see FIGS. 7 and 8) in which the two-dimensional plane on which the medical care data is displayed is three-dimensionally displayed using the laws of perspective.

The item name display region 42 is disposed at the right end of the main display region 41. An item name of medical care data displayed in each sub region 41A is displayed in the item name display region 42. In the item name display region 42, category names to which each data name belongs, such as vital, specimen examination, image examination, medication, or injection, are also displayed, in addition to item names such as a body temperature, a blood pressure (upper), a blood pressure (lower), white blood cells, CT examination, or S injection.

Two time axes of a first time axis 51 and a second time axis 52 are provided on the display screen 15. The first time axis 51 is provided above the main display region 41, and the second time axis 52 is provided at an upper end in the main display region 41. The second time axis 52 is a time axis indicating a display period in the main display region 41. The second time axis 52 has a width in the longitudinal direction, in which numerals indicating a year, a month and a date, and a scale set per day are displayed. In FIG. 6, in the main display region 41, medical care data corresponding to one month of August 2014 is displayed, and correspondingly, medical care data corresponding to about one month of August 2014 is displayed on the second time axis 52.

On the other hand, on the first time axis 51, a relatively long display period may be displayed, compared with the second time axis 52. In the two-dimensional display mode, the first time axis 51 is set to a relatively long display period, compared with the second time axis 52. In the example of FIG. 6, a display period of the second time axis 52 is set to about one month of August 2014, whereas a display period of the first time axis 51 is set to about three months from June 2014 to August 2014. Similar to the second time axis 52, the first time axis 51 has a width in the height direction, in which numerals indicating a year and a month, and a scale for dividing a period at a predetermined interval are displayed.

On the first time axis 51, an existence mark 51A indicating a period during which medical care data exists may be displayed. Through the existence mark 51A, it is possible to check the period during which the medical care data exists in the display period of the first time axis 51. Further, on the first time axis 51, if an arbitrary time is designated using the pointer 35, medical care data at the arbitrary time can be displayed in the main display region 41. For example, on the first time axis 51, if the existence mark 51A of June 2014 is designated using the pointer 35, the display period displayed in the main display region 41 is changed from August 2014 to June 2014.

Further, in the main display region 41, a reference numeral 53 represents a compression mark indicating a compression period. In the case of a patient who is not hospitalized but is receiving medical treatment as an outpatient, or in the case of a patient who repeatedly enters and leaves a hospital, a blank period during which there is no medical care data occurs. In the blank period during which there is no medical care data, only a blank is displayed in the main display region 41, so that the display space is merely wasted. Thus, in the main display region 41, with respect to the blank period during which there is no medical care data, the display period is compressed in the time axis direction, and the compressed mark 53 is displayed therefor. The compressed mark 53 is displayed in such a form that the interval between the vertical grid lines 48 is narrowed to become compact, for example. In this example, since a period from August 11, 2014 to August 17 is a blank period of medical care data, the compressed mark 53 is displayed for the blank period. Thus, it is possible to effectively use the limited main display region 41.

In addition, a display magnification change unit 54 for changing a magnification for displaying the main display region 41 is provided on the right side of the second time axis 52 and above the item name display region 42. The display magnification change unit 54 enlarges or reduces a display magnification of the entire main display region 41 by a slide operation of a slider in a plus direction (enlarging direction) or a minus direction (reduction direction).

By enlarging the display magnification, it is possible to display the polygonal line graph G or the thumbnail image TP in the main display region 41 in an enlarged size. Contrarily, in the transverse direction, the display period is shortened, and the number of data items displayed in the longitudinal direction decreases. On the other hand, if the display magnification is reduced, the polygonal line graph G or the thumbnail image TP in the main display region 41 is displayed in a reduced size, but contrarily, the display period is lengthened, and the number of data items to be displayed increases.

Further, a display mode switching button 56 is provided above the first time axis 51. The display mode switching button 56 is an operation unit for inputting an operation instruction of switching of the display mode of the main display region 41 between the two-dimensional display mode and the three-dimensional display mode, and is operated by a click operation of a mouse through the pointer 35.

In the two-dimensional display mode, as shown in FIG. 6, the main display region 41 is displayed on the two-dimensional plane formed by two axes of the time axis (transverse axis) and the data array axis (longitudinal axis). In the two-dimensional display mode, medical care data (time series data) is displayed on this two-dimensional plane. In this state, if the display mode switching button 56 is operated, the display mode of the main display region 41 is switched into the three-dimensional display mode shown in FIG. 7.

Figure 7:
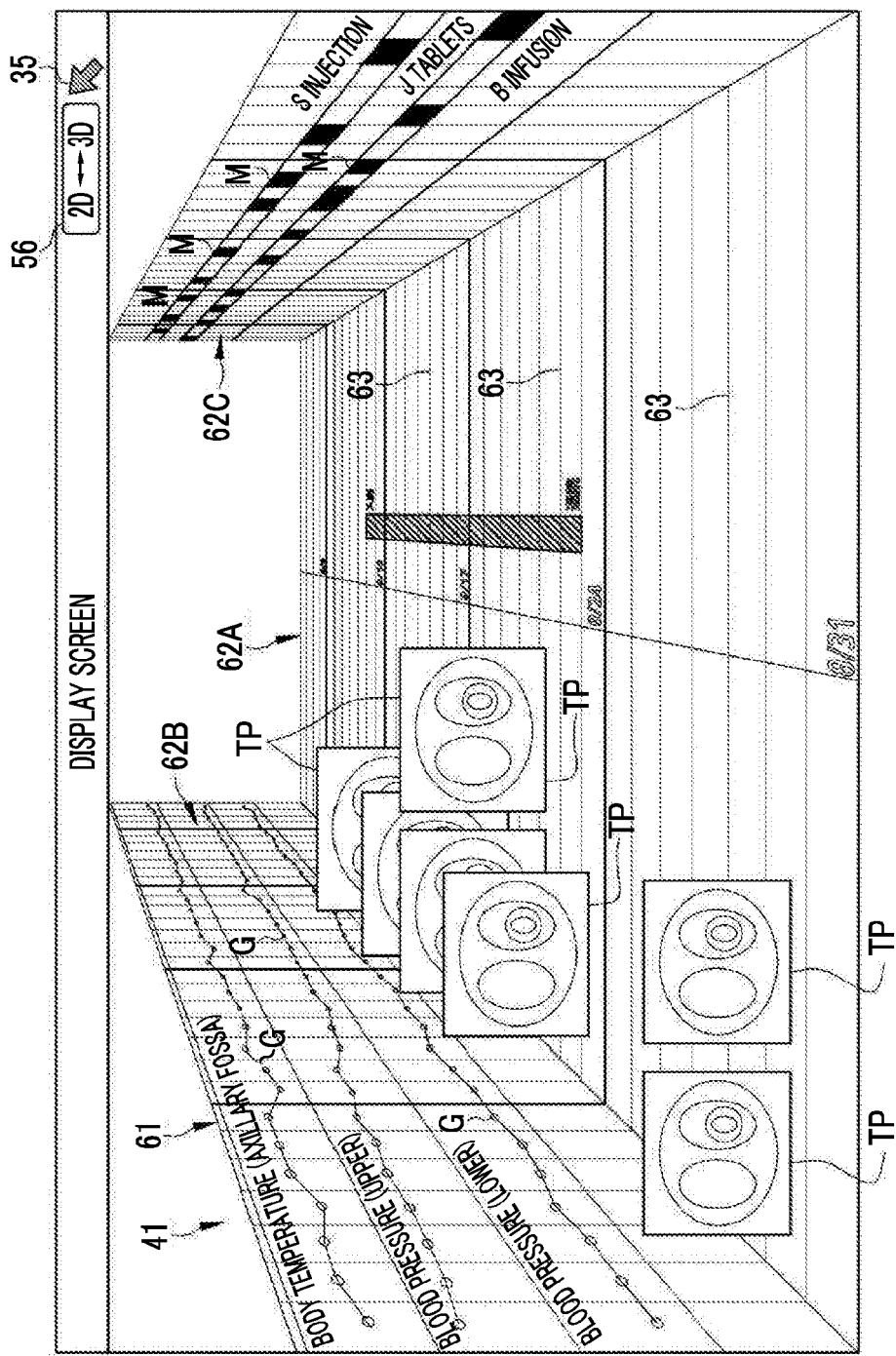
FIG. 7 is a diagram illustrating an example of a display screen in a three-dimensional display mode.

As shown in FIG. 7, the three-dimensional display mode is a display mode in which the main display region 41 which is a two-dimensional plane on which medical care data (time series data) is displayed is three-dimensionally displayed, using the laws of perspective by which a plurality of straight lines parallel to the time axis in the two-dimensional display mode are drawn to be converged toward the past on the time axis. In this example, in the three-dimensional display mode, a virtual rectangular box 61 having a longitudinal direction that coincides with the time axis and displayed by the laws of perspective is set as the main display region 41, and a plurality of pieces of medical care data (time series data) are displayed on at least a part of an inner circumferential surface 62 of the rectangular box 61. Such a virtual three-dimensional process may be performed using an image processing technique for setting a virtual three-dimensional space and allocating data on a two-dimensional plane in the set three-dimensional space, for example.

In this example, the inner circumferential surface 62 is formed by three surfaces of a bottom surface 62A disposed on a bottom side of the display screen 15, and both side surfaces 62B and 62C that rise vertically from both ends of the bottom surface 62A. The time axis is disposed in the longitudinal direction of the rectangular box 61, in which the front side of the rectangular box 61 is the current direction and the back side thereof is the past direction in FIG. 7.

In the three-dimensional display mode, a time scale of the main display region 41 is set so that the time scale is slightly lengthened compared with the two-dimensional display mode. Thus, in the three-dimensional display mode, the display period of medical care data (time series data) is lengthened compared with the two-dimensional display mode. In this example, in the two-dimensional display mode shown in FIG. 6, the display period of the main display region 41 is substantially 20 days since about one week in the middle of about one month of August 2014 is compressed. On the other hand, in the three-dimensional display mode shown in FIG. 7, the display period is 31 days since about one month of August 2014 is displayed without compression. Further, by setting a difference between the time scale in the two-dimensional display mode and the time scale in the three-dimensional display mode to be larger than that in this example, the time scale in the three-dimensional display mode may be set to be relatively long.

If the time scale in the three-dimensional display mode is set to be long, as the time goes farther to the past, the display magnification is more reduced and the display size becomes smaller, but compared with a case where the past time and the current time are switched by a screen scroll operation in the two-dimensional display for display, it is possible to easily recognize a long-term tendency of medical care data at a glance.

Particularly, by combining the laws of perspective and the prolonged time scale, it is possible to recognize an entire tendency over a long period due to a synergistic effect with the laws of perspective. Thus, using the two-dimensional display mode in recognition of short-term changes in time series data and details thereof, and using the three-dimensional display mode in recognition of an entire tendency over a long period, it is possible to check short-term and long-term time series data using a simple operation while reducing a screen scroll operation.

Even in the three-dimensional display mode, similar to the two-dimensional display mode, a period during which there is no medical care data may be compressed in the time axis direction to be displayed.

Grid lines 63 provided in a daily basis are displayed on the inner circumferential surface 62, for example. Time series data of respective items of a date and time display, an ambulatory care history, and a CT examination is allocated and displayed on the bottom surface 62A. Thumbnail images TP of the CT examination are enlarged and displayed compared with those in the two-dimensional display mode, for example. The thumbnail images TP are disposed at positions corresponding to photographing dates. Further, the thumbnail images TP are two-dimensionally displayed to have postures rising from the bottom surface 62A so that their drawing surfaces face the front.

Respective polygonal line graphs G of a body temperature, a blood pressure (upper), and a blood pressure (lower) are displayed on the left side surface 62B. Marks M indicating that S injection, J tablets, B infusion, and the like are administered are displayed on the left side surface 62C. In this way, by setting the rectangular box 61 and setting the inner circumferential surface 62 formed by three surfaces of the bottom surface 62A, the both side surfaces 62B and 62C as a region where data items are allocated, it is possible to enlarge a region where data items are allocated, compared with the two-dimensional display.

If the region where the data items are allocated is enlarged, since the data items capable of being displayed increase, it is possible to generally recognize the tendency of a plurality of pieces of medical care data (time series data) with ease. That is, perspicuity with respect to the tendency of a plurality of pieces of medical care data is enhanced. Further, since the region where the data items are allocated is enlarged, overlapping of a plurality of pieces of medical care data is reduced, and visibility is enhanced. An item name of each piece of medical care data is displayed on the bottom surface 62A, and the both side surfaces 62B and 62C, respectively, similar to the medical care data.

In addition, since the bottom surface 62A, and the both side surfaces 62B and 62C form the inner circumferential surface 62 of the rectangular box 61, each of them is formed by a plane, unlike a cylinder. Thus, as indicated by the grid lines 63, data array axes on which respective data items are arrayed on each surface are straight lines. Unlike the cylinder, since the data array axes are straight lines, the medical care data (time series data) is easily viewed. Similarly, since a data fluctuation direction of the polygonal line graph G is also a straight line, fluctuation in data values is easily recognized, compared with the cylinder in which a data fluctuation direction is curved.

Further, since the rectangular box 61 is displayed by the laws of perspective, a plurality of straight lines parallel to the time axis, which form the rectangular box 61, are converged at one vanishing point that exists in the past direction. Depending on a place where the vanishing point is set, a display angle of the rectangular box 61 is changed. For example, if the vanishing point is moved upward, the inclination of the bottom surface 62A is further increased, and if the vanishing point is moved rightward, the left side surface 62B is positioned in a state close to a two-dimensional display, to thereby enhance visibility. Of course, if the vanishing point is moved rightward, the right side surface 62C becomes difficult to see, contrary to the left side surface 62B.

In addition, in this example, the inner circumferential surface 62 of the rectangular box 61 is configured by only three surfaces of the bottom surface 62A, and the both side surfaces 62B and 62C, in which a ceiling surface is not provided. However, the ceiling surface may be provided, and medical care data may also be displayed on the ceiling surface.

However, as a result of verification in a case where there is a ceiling surface and in a case where there is no ceiling surface, it is shown that it is easier to view medical care data in a case where the ceiling surface is not provided and the medical care data is displayed on only the three surfaces of the bottom surface 62A, and the both side surfaces 62B and 62C as in this example, compared with a case where the ceiling surface is provided and medical care data is displayed around the entire circumference including the ceiling surface of the inner circumferential surface 62.

It is considered that the reason is because if a ceiling surface is provided, the array position of medical care data is excessively distracted and it is difficult to set all of four surfaces including the ceiling surface at angles where the medical care data can be easily viewed. If the display angle of the rectangular box 61 is set to a display angle at which the bottom surface 62A is easily viewed, the ceiling surface becomes difficult to see. Accordingly, it is difficult to set all the four surfaces at angles where the medical care data can be easily viewed. Thus, in this example, the ceiling surface is not provided, and only three surfaces of the bottom surface 62A, the both side surfaces 62B and 62C are used.

Figure 8:
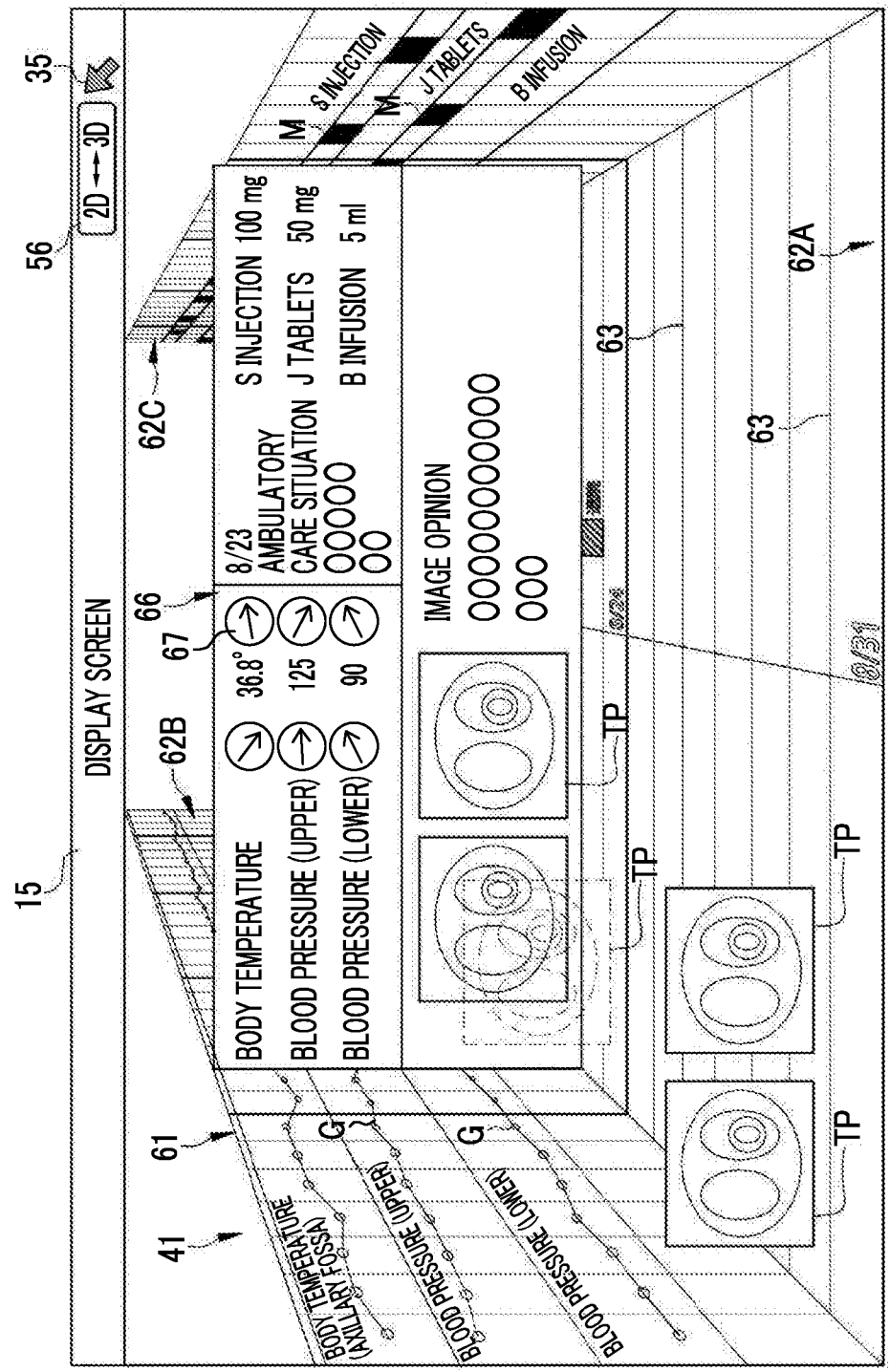
FIG. 8 is a diagram illustrating a summary window in the three-dimensional display mode.

Further, as shown in FIG. 8, in the three-dimensional display mode, a summary window 66 for displaying a summary of content of each of a plurality of pieces of medical care data (time series data) at a designated point in time on the time axis may be displayed. The summary window 66 is displayed in the form of a two-dimensional plane developed in a direction orthogonal to the time axis, at an arbitrary point in time designated on the time axis, for example. In this example, the summary window 66 displays a summary of data content of a plurality of pieces of medical care data on August 23. On August 23, there are data items of a body temperature, a blood pressure (upper), a blood pressure (lower), CT examination, S injection, J tablets, and B infusion as the plurality of pieces of medical care data, and a summary of data content of the plurality of data items is displayed in the summary window 66.

More detailed content than the content of the data displayed on the inner circumferential surface 62 is displayed in the summary window 66. For example, in the case of body temperature, blood pressure (upper), and blood pressure (lower), specific data values thereof and indicators 67 indicating the tendencies before and after August 23 which is a reference date are displayed. Each indicator 67 is an arrow display, for example. Depending on the direction of the arrow, it is possible to display whether the data value is decreasing or increasing, and further, to display the degree of decrease or increase by an inclination of the arrow. Further, for a data item such as medication or injection, in addition to a medicine name, its dose is displayed as specific numerical value data. In addition, a comment indicating a status of an ambulatory care on August 23 is displayed. With respect to the CT examination, in addition to the thumbnail images TP, an image opinion of a doctor is also displayed.

The summary window 66 may be displayed by designating a grid line 63 at an arbitrary point in time (date) on the time axis using the pointer 35, for example, and performing a click operation using a mouse. Contrarily, if the summary window 66 is designated using the pointer 35 and a click operation is performed, the summary window 66 may be hidden.

By displaying the summary window 66 in this way, even in the three-dimensional display, it is possible to easily recognize data content of a plurality of pieces of medical care data (time series data). A method for displaying the plurality of medical care data on the inner circumferential surface 62 of the rectangular box 61 enlarges the allocation region of the plurality of pieces of medical care data, perspicuity with respect to the tendency of the plurality of pieces of medical care data (time series data) is enhanced. However, since medical care data is dispersed on the bottom surface 62A, and the both side surfaces 62B and 62C, respectively, it is difficult to recognize data content at an arbitrary point in time. Thus, by displaying the summary window 66, it is possible to compensate for a drawback in the three-dimensional display using the inner circumferential surface 62 of the rectangular box 61, and thus, it is possible to simply recognize data content.

In determination of a medical care policy, since a determination is made focusing on the relationship between a plurality of data items of medical care data, it is highly necessary to easily recognize the content of the plurality of data items at an arbitrary point in time. The summary window 66 is particularly useful when applied to the display screen 15 of the medical care data.

Further, in this example, in a case where the summary window 66 and a thumbnail image TP disposed in the current direction with reference to a display date of the summary window 66 overlap each other, the thumbnail image TP (indicated by a broken line in FIG. 8) is displayed in a semi-transparent form. With this configuration, it is possible to prevent the display of the summary window 66 from being hidden by the thumbnail image TP while showing that the thumbnail image TP exists in the current direction with reference to the date of the summary window 66.

Hereinafter, operations according to the configuration will be described with reference to a flowchart shown in FIG. 9. A doctor who treats a patient views medical care data through the client terminal 12. The doctor starts up viewer software of the client terminal 12, designates a patient ID, and inputs a distribution instruction of medical care data (S (step) 1010).

Thus, a distribution request issued from the request issuing unit 34 of the client terminal 12 is transmitted to the medical care support server 11. The medical care support server 11 inputs, if the request receiving unit 36 receives the distribution request, the distribution request to the screen data generating unit 37. The screen data generating unit 37 transmits an acquisition request of medical care data of the designated patient ID to the server group 13, and acquires the medical care data (S2010).

In the medical care support server 11, the screen data generating unit 37 generates screen data of the display screen 15 on the basis of the acquired medical care data (S2020). The screen editing unit 38 edits the screen data as necessary, and inputs the screen data to the output control unit 39. The output control unit 39 distributes the screen data to the client terminal 12 which is a request source through the communication I/F 24 (S2030).

If the screen data is received, the client terminal 12 reproduces the display screen 15 shown in FIG. 6, for example, on the basis of the screen data received by the GUI control unit 33, and displays the result on the display 28A (S1020). In the display screen 15 shown in FIG. 6, since the main display region 41 is displayed in the two-dimensional display mode, in a case where the doctor wants to display the main display region 41 in the three-dimensional display mode as shown in FIGS. 7 and 8, the doctor operates the display mode switching button 56.

If the display mode switching operation (screen editing operation) is made (Y in S1030), the request issuing unit 34 issues an editing request on the basis of a screen editing request (S1040). The editing request is transmitted to the medical care support server 11. In the medical care support server 11, if the editing request is received, the request receiving unit 36 inputs the editing request to the screen editing unit 38. The screen editing unit 38 performs a screen display control for switching the screen data of the display screen 15 from the two-dimensional display mode into the three-dimensional display mode by a screen editing process (S2040). The screen data after editing is distributed to the client terminal 12 which is the request source by the output control unit 39 (S2050).

If the screen data after editing is received, the client terminal 12 reproduces and displays the display screen 15 on the basis of the screen data after editing (S1050). Thus, the doctor can view the main display region 41 in the three-dimensional display mode. In the three-dimensional display mode, the virtual rectangular box 61 having a longitudinal direction that coincides with the time axis and displayed by the laws of perspective is set as the main display region 41, and a plurality of medical care data (time series data) are displayed on the inner circumferential surface 62 of the rectangular box 61. In this way, by setting the rectangular box 61 and setting the inner circumferential surface 62 formed by three surfaces of the bottom surface 62A, and the both side surfaces 62B and 62C as a region where data items are allocated, it is possible to enlarge a region where data items are allocated, compared with the two-dimensional display. Thus, perspicuity with respect to the tendency of a plurality of pieces of medical care data (time series data) is enhanced.

Further, by performing a click operation with respect to a grid line 63 at an arbitrary point in time on the time axis, as shown in FIG. 8, it is possible to display the summary window 66. By displaying the summary window 66, even in the three-dimensional display, it is possible to easily recognize data content of a plurality of medical care data (time series data). By using the three-dimensional display using the inner circumferential surface 62 of the rectangular box 61 and the summary window 66 together, it is possible to easily recognize data content of a plurality of pieces of medical care data (time series data) even in the three-dimensional display while securing perspicuity with respect to the tendency of the plurality of pieces of medical care data.

In determination of a medical care policy, since a determination is made focusing on the relationship between a plurality of data items of medical care data, it is highly necessary to easily recognize the content of the plurality of data items at an arbitrary point in time. The summary window 66 is particularly useful when applied to the display screen 15 of the medical care data. Further, in the medical care, it is necessary to perform recognition of medical care data from various points of view such as general recognition of the tendency of a plurality of pieces of medical care data or recognition of detailed data content or change thereof. According to this embodiment, it is possible to respond to such a request.

Further, in the three-dimensional display mode, a time scale of the main display region 41 is longer than that in the two-dimensional display mode, and thus, it is possible to view medical care data over a long period. If the time scale of the three-dimensional display mode is further lengthened, it is possible to recognize the tendency of medical care data over a longer period.

For the medical care data, in many cases, a medical care of a patient is performed over a long period, or a medical care is intermittently performed while a patient repeatedly enters and leaves a hospital. In such a case, an acquisition period of medical care data becomes long. It is natural that long-term medical care data has a long time axis. The medical care data is used by a doctor for use in determining a medical care policy of a patient. In determination of the medical care policy, it is important to recognize both of the presence or absence of a short-term change of time series data relating to a medical care or details thereof and an overall tendency over a long period.

According to this embodiment, it is possible to view medical care data both in the two-dimensional display mode and in the three-dimensional display mode with a time scale longer than that in the two-dimensional display mode. In the two-dimensional display mode, since medical care data is displayed on a two-dimensional plane, the presence or absence of change in data values for a short period and details thereof are easily checked. On the other hand, in the three-dimensional display mode with a long time scale, while it is difficult to check a detailed change in data values, it is possible to suitably recognize an overall tendency over a long period. The switching between two display modes of the two-dimensional display mode and the three-dimensional display mode can be easily performed by an operation of the display mode switching button 56, for example. Thus, a doctor can easily recognize both of the presence or absence of a short-term change of medical care data of a patient and details thereof and an overall tendency over a long period, using both the two display modes.

Figure 9:
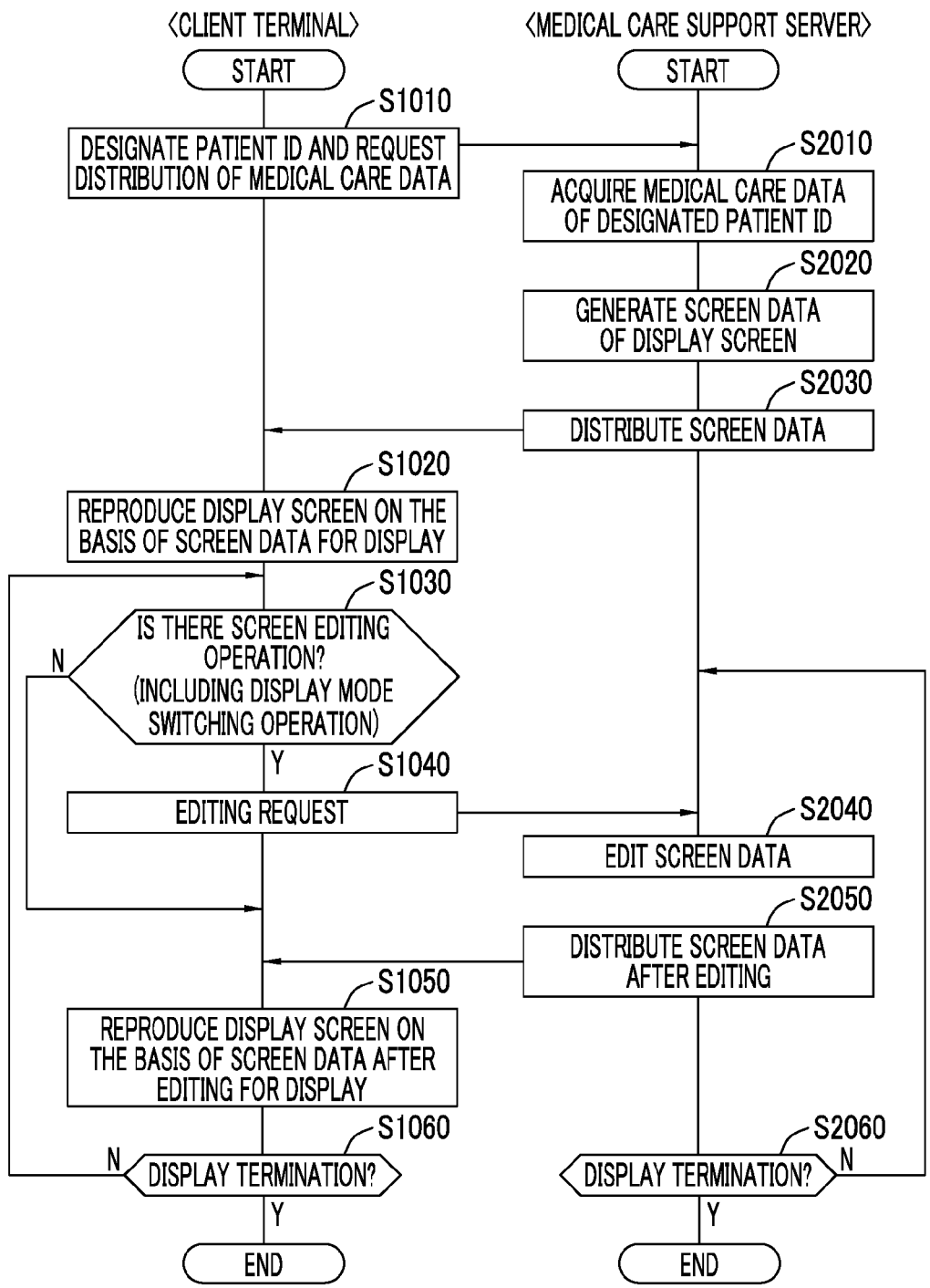
FIG. 9 is a flowchart illustrating a processing procedure.

In FIG. 9, the client terminal 12 repeats the above-described steps until there is a display termination instruction (Y in S1060). For example, in a case where an operation for returning to the two-dimensional display mode from the three-dimensional display mode or another editing operation such as an additional data request is performed, the client terminal 12 transmits a distribution request or an editing request based on such an operation to the medical care support server 11. In the medical care support server 11, in a case where there is the additional data distribution request or another editing request from the client terminal 12, the screen editing unit 38 performs an editing process, and distributes screen data after editing. The medical care support server 11 repeats the editing process until there is a display termination instruction in the client terminal 12 (Y in S1060 and Yin S2060).

In the three-dimensional display mode of this example, the virtual rectangular box 61 having a longitudinal direction that coincides with the time axis and displayed by the laws of perspective is set as the main display region 41, and a plurality of pieces of medical care data (time series data) are displayed on at least a part of the inner circumferential surface 62 of the rectangular box 61. Thus, compared with the three-dimensional display using the circumferential surface of the virtual cylinder disclosed in JP1994-243264A (JP-H6-243264A), the data array axis on which the plurality of pieces of medical care data (time series data) are allocated is not curved, and thus, the medical care data (time series data) is easily viewed. Particularly, since a fluctuation direction of data values of the time series data and the data array axis coincide with each other, fluctuation of the data values is also easily recognized.

Further, in the three-dimensional display mode of this example, since the summary window 66 for displaying a summary of content of each of a plurality of pieces of medical care data (time series data) at a designated point in time on the time axis is displayed, even in the three-dimensional display, it is possible to easily recognize data content of the plurality of pieces of medical care data (time series data).

In this embodiment, an example in which the three-dimensional display mode in which the virtual rectangular box 61 is set is combined with the summary window 66 is shown, but instead of the rectangular box 61, a configuration in which a three-dimensional display mode in which a cylinder is set as disclosed in JP1994-243264A (JP-H6-243264A) and the summary window 66 are combined may be used. Of course, as described above, since the rectangular box 61 has many advantages compared with the cylinder, it is preferable that the three-dimensional display mode in which the rectangular box 61 is set as described in this embodiment and the summary window 66 are combined.

Further, in this embodiment, an example in which the summary window 66 is provided in the form of a two-dimensional plane developed in a direction orthogonal to the time axis at a point in time designated on the time axis is shown, but another form may be used. For example, the display position may not be the designated point in time on the time axis. Even in this case, since the summary window 66 needs to indicate that data content is displayed a certain point in time, it is necessary to provide a link display for linking the summary window 66 and a designated point in time. Of course, as described in this embodiment, if the summary window 66 is displayed at a designated point in time, the link display is not necessary, and thus, it is preferable to display the summary window 66 as in this embodiment.

In addition, an example in which the summary window 66 is provided in the form of a two-dimensional plane is shown, but the summary window 66 may be provided in the form of a virtual three-dimensional display. Of course, in a case where a data value or a comment is to be checked, the two-dimensional plane shows better visibility, and thus, it is preferable that the summary window 66 is provided in the form of a two-dimensional plane as in this embodiment.

[Second Embodiment]

Figure 10:
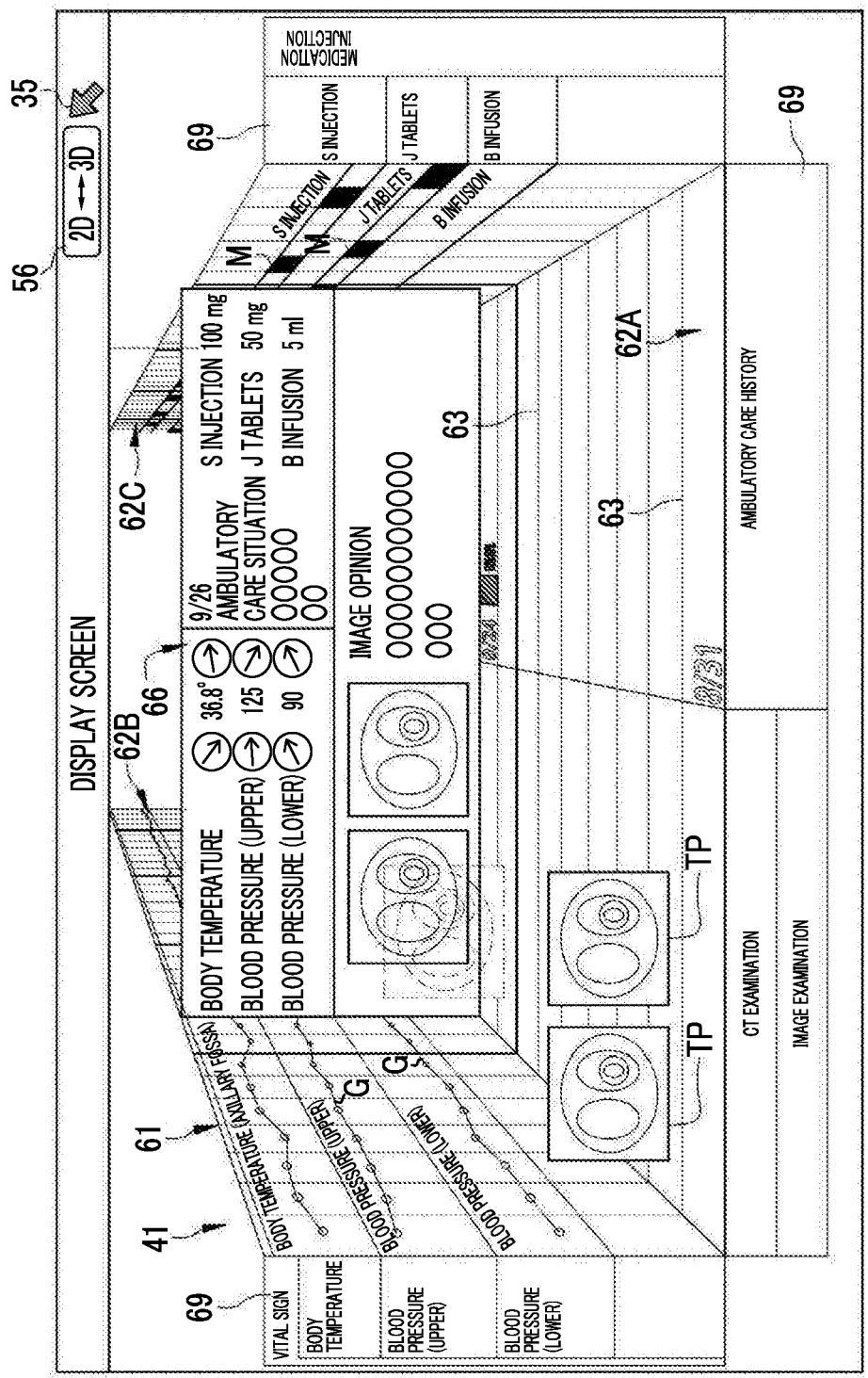
FIG. 10 is a diagram illustrating a display screen in a three-dimensional display mode according to a second embodiment.

As in a second embodiment shown in FIG. 10, in the three-dimensional display mode, an item name display region 69 which is two-dimensionally displayed may be provided. This makes it easier to check item names. Further, the item name display region 69 is disposed at an end in the current direction on the time axis, in the main display region 41 formed by the rectangular box 61. In the three-dimensional display mode, the inner circumferential surface 62 of the rectangular box 61 is configured to have a large display magnification along the current direction. Thus, by disposing the item name display region 69 at the end in the current direction, it is possible to increase the display magnification of the item name display region 69, and thus, it is possible to easily check the item names.

[Third Embodiment]

Figure 11:
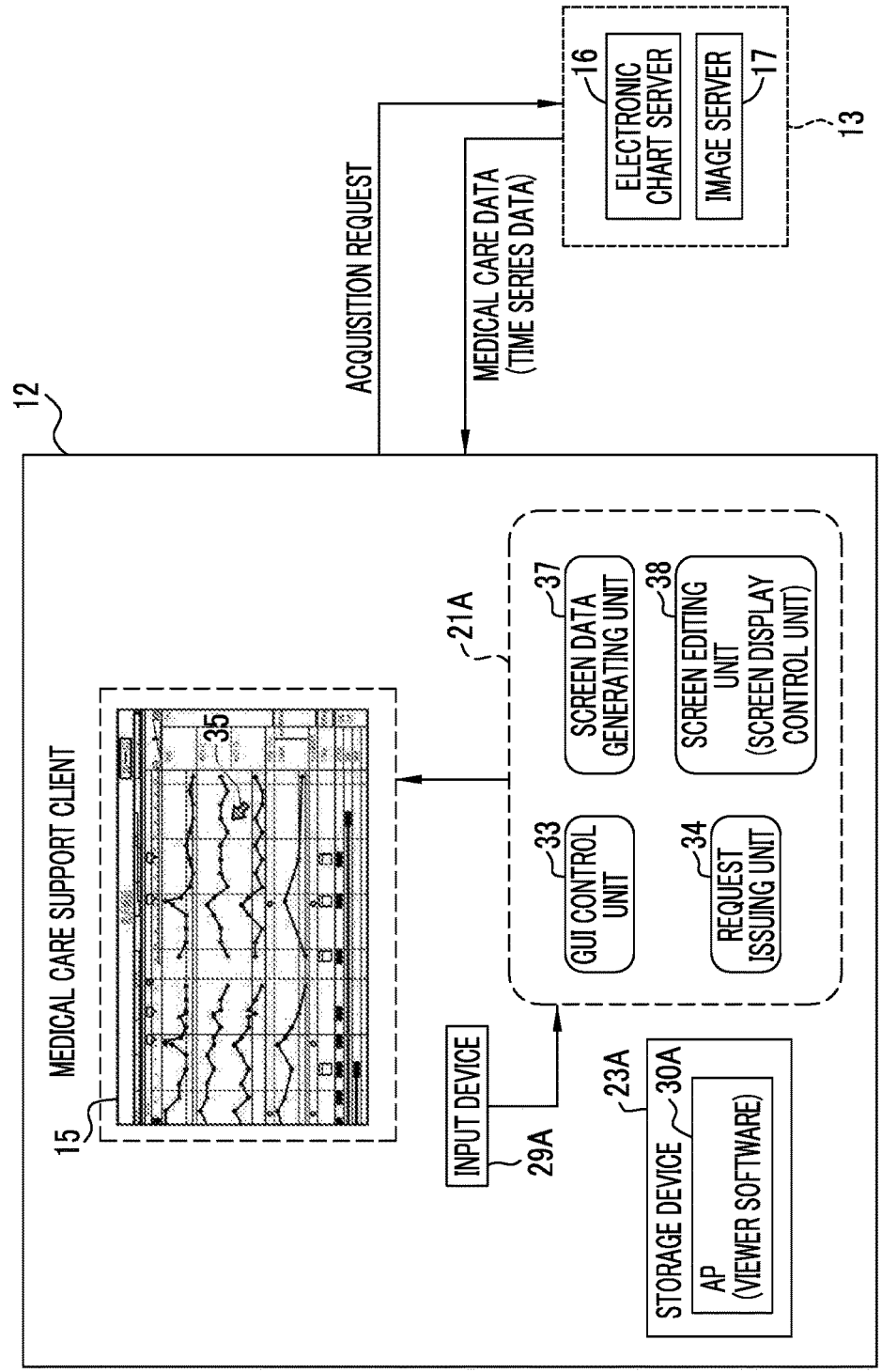
FIG. 11 is a diagram illustrating a client terminal according to a third embodiment.

In the above-described respective embodiments, an example in which the time series data display control device of the invention is provided in the form of the medical care support server 11 that distributes screen data of the display screen 15 on the basis of a request of the client terminal 12 is shown, but as shown in FIG. 11, a configuration in which the client terminal 12 functions as a time series data display control device may be used. In FIG. 11, the same reference numerals are given to the same portions as in the above-described embodiments, and description thereof will not be repeated.

The third embodiment is different from the first embodiment in that the CPU 21A executes the viewer software of the client terminal 12 to function as the screen data generating unit 37 and the screen editing unit 38.

In the client terminal 12, the screen data generating unit 37 directly accesses the server group 13 to obtain medical care data and to generate screen data of the display screen 15. The GUI control unit 33 reproduces the display screen 15 on the basis of the generated screen data, and displays the result on the display 28A. The screen editing unit 38 performs a screen display control for switching between the two-dimensional display mode and the three-dimensional display mode with respect to a display mode of the display screen 15 on the basis of a display mode switching instruction. In the third embodiment, the viewer software functions as a time series data display control program.

In this way, the time series data display control device is not limited to the form of the medical care support server 11 that distributes screen data as in the first embodiment, and may have the form of the client terminal 12 as in the third embodiment.

Further, for example, as in a form in which generation of screen data is performed in the medical care support server 11 and the screen display control function for switching between the two-dimensional display mode and the three-dimensional display mode is performed in the client terminal 12, a part of the screen data generation function and the screen display control function may be performed on the medical care support server 11, and the other part thereof may be performed on a part of the client terminal 12. In this case, a computer system configured by the client terminal 12 and the medical care support server 11 functions as a time series data display control system.

As described above, the time series data display control device and system of the invention may be realized by various forms. Further, a hardware configuration of a computer system such as the medical care support server 11, the client terminal 12 may have various modifications. For example, the medical care support server 11 may be configured by a plurality of server computers separated as hardware for the purpose of improving its processing capacity and reliability. In this way, the hardware configuration of the computer system may be appropriately modified according to required performance such as a processing capacity, safety, or reliability. Further, the modification is not limited to the hardware configuration, and the time series data display control program may be duplicated, or may be dividedly stored in a plurality of storage devices in order to secure safety or reliability.

In addition, in the above-described respective embodiments, a form in which the medical care support server 11 and the client terminals 12 are used in one medical care facility is described, but for example, a form in which one medical care support server 11 is provided in an external data center and an application service such as a data distribution service of the medical care support server 11 in the data center can be used in the client terminals 12 in a plurality of medical care facilities may be used.

In this case, the medical care support server 11 is connected to the client terminals 12 provided in the plurality of medical care facilities to be communicable therewith through a wide area network (WAN) such as the Internet or a public communication network, for example. Further, the medical care support server 11 receives a request from each of the client terminals 12 in the plurality of medical care facilities, and provides an application service such as distribution of screen data of the display screen 15 to each client terminal.

For example, an installation location or an operation entity of the data center and the medical care support server 11 may be, for example, one of a plurality of medical care facilities, or may be a service company other than the medical care facilities. Further, in a case where a WAN such as a network is used, it is preferable to construct a virtual private network (VPN), or to use a communication protocol with a high security level such as Hypertext Transfer Protocol Secure (HTTPS) in consideration of information security.

Further, in the above-described respective embodiments, an example in which medical care data is used as time series data is shown, but the invention may be applied to time series data other than the medical care data. Even in the time series data other than the medical care data, in a case where both a two-dimensional display and a three-dimensional display are performed, and in a case where it is necessary to easily recognize data content of a plurality of pieces of time series data at a point in time even in the three-dimensional display, the invention is usefully applied. With respect to medical care data, since such a necessity is high as described above, the invention is particularly useful.

The invention is not limited to the above-described embodiments, and may have various configurations without departing from the concept of the invention. For example, appropriate combinations of the above-described various embodiments or various modified examples may be used. Further, the invention is applied, in addition to a program, to a storage medium that stores the program.

EXPLANATION OF REFERENCES

- 11: medical care support server
- 12: client terminal
- 15: display screen
- 37: screen data generating unit
- 38: screen editing unit (screen display control unit)
- 39: output control unit
- 41: main display region
- 42, 69: item name display region
- 51: first time axis
- 52: second time axis
- 56: display mode switching button
- 61: rectangular box
- 62: inner circumferential surface
- 62A: bottom surface
- 62B, 62C: side surface
- 66: summary window

What is claimed is:

1. A time series data display control device comprising a processor configured to:
    generate a time series data display screen on which a plurality of pieces of time series data are displayed; and
    perform switching between display modes of the time series data display screen, in which the display modes include two display modes of a two-dimensional display mode in which the time series data is displayed on a two-dimensional plane formed by two axes of a time axis of the plurality of pieces of time series data and a data array axis orthogonal to the time axis, on which the plurality of pieces of time series data are arrayed, and a three-dimensional display mode in which the two-dimensional plane is three-dimensionally displayed using the laws of perspective by which a plurality of straight lines parallel to the time axis in the two-dimensional display mode are drawn to be converged toward the past on the time axis,
    wherein in the three-dimensional display mode, the processor is able to display a summary window for displaying a summary of data content of the plurality of pieces of time series data at a designated point in time on the time axis,
    wherein the summary window is provided in the form of a two-dimensional plane developed in a direction orthogonal to the time axis at an arbitrary point in time designated on the time axis.

2. The time series data display control device according to claim 1,
    wherein in the three-dimensional display mode, a virtual rectangular box having a longitudinal direction that coincides with the time axis and displayed by the laws of perspective is set in the time series data display screen, and the plurality of pieces of time series data are displayed on at least a part of an inner circumferential surface of the rectangular box.

3. The time series data display control device according to claim 2,
    wherein the inner circumferential surface is formed by three surfaces of a bottom surface, and both side surfaces rising from both ends of the bottom surface.

4. The time series data display control device according to claim 3,
    wherein in the three-dimensional display mode, an item name display region indicating respective item names of the plurality of pieces of time series data is two-dimensionally displayed.

5. The time series data display control device according to claim 4,
    wherein on the time series data display screen, the item name display region is disposed at the end of the current direction on the time axis.

6. The time series data display control device according to claim 3,
    wherein on the time series data display screen, a period during which the time series data does not exist is compressed in the time axis direction to be displayed.

7. The time series data display control device according to claim 2,
    wherein in the three-dimensional display mode, an item name display region indicating respective item names of the plurality of pieces of time series data is two-dimensionally displayed.

8. The time series data display control device according to claim 7,
    wherein on the time series data display screen, the item name display region is disposed at the end of the current direction on the time axis.

9. The time series data display control device according to claim 8,
    wherein on the time series data display screen, a period during which the time series data does not exist is compressed in the time axis direction to be displayed.

10. The time series data display control device according to claim 7,
    wherein on the time series data display screen, a period during which the time series data does not exist is compressed in the time axis direction to be displayed.

11. The time series data display control device according to claim 2, wherein on the time series data display screen, a period during which the time series data does not exist is compressed in the time axis direction to be displayed.

12. The time series data display control device according to claim 2,
wherein the time series data is medical care data relating to a medical care of a patient.

13. The time series data display control device according to claim 1,
wherein on the time series data display screen, a period during which the time series data does not exist is compressed in the time axis direction to be displayed.

14. The time series data display control device according to claim 1,
wherein on the time series data display screen, a period during which the time series data does not exist is compressed in the time axis direction to be displayed.

15. The time series data display control device according to claim 1,
wherein the time series data is medical care data relating to a medical care of a patient.

16. The time series data display control device according to claim 1,
wherein the time series data is medical care data relating to a medical care of a patient.

17. A method for operating a time series data display control device, comprising:
a screen data generating step of generating a time series data display screen on which a plurality of pieces of time series data are displayed; and
a screen display control step of performing switching between display modes of the time series data display screen, in which the display modes include two display modes of a two-dimensional display mode in which the time series data is displayed on a two-dimensional plane formed by two axes of a time axis of the plurality of pieces of time series data and a data array axis orthogonal to the time axis, on which the plurality of pieces of time series data are arrayed, and a three-dimensional display mode in which the two-dimensional plane on which the time series data is displayed is three-dimensionally displayed using the laws of perspective by which a plurality of straight lines parallel to the time axis in the two-dimensional display mode are drawn to be converged toward the past on the time axis,
wherein in the screen display control step, a summary window for displaying a summary of data content of the plurality of pieces of time series data at a designated point in time on the time axis is able to be displayed in the three-dimensional display mode,
wherein the summary window is provided in the form of a two-dimensional plane developed in a direction orthogonal to the time axis at an arbitrary point in time designated on the time axis.

18. A non-transitory computer readable recording medium storing a time series data display control program that causes a computer to function as a time series data display control device, comprising:
a screen data generating step of generating a time series data display screen on which a plurality of pieces of time series data are displayed; and
a screen display control step of performing switching between display modes of the time series data display screen, in which the display modes include two display modes of a two-dimensional display mode in which the time series data is displayed on a two-dimensional plane formed by two axes of a time axis of the plurality of pieces of time series data and a data array axis orthogonal to the time axis, on which the plurality of pieces of time series data are arrayed, and a three-dimensional display mode in which the two-dimensional plane on which the time series data is displayed is three-dimensionally displayed using the laws of perspective by which a plurality of straight lines parallel to the time axis in the two-dimensional display mode are drawn to be converged toward the past on the time axis,
wherein in the screen display control step, a summary window for displaying a summary of data content of the plurality of pieces of time series data at a designated point in time on the time axis is able to be displayed in the three-dimensional display mod,
wherein the summary window is provided in the form of a two-dimensional plane developed in a direction orthogonal to the time axis at an arbitrary point in time designated on the time axis.

19. A time series data display control system comprising a processor configured to:
generate a time series data display screen on which a plurality of pieces of time series data are displayed; and
perform switching between display modes of the time series data display screen, in which the display modes include two display modes of a two-dimensional display mode in which the time series data is displayed on a two-dimensional plane formed by two axes of a time axis of the plurality of pieces of time series data and a data array axis orthogonal to the time axis, on which the plurality of pieces of time series data are arrayed, and a three-dimensional display mode in which the two-dimensional plane on which the time series data is displayed is three-dimensionally displayed using the laws of perspective by which a plurality of straight lines parallel to the time axis in the two-dimensional display mode are drawn to be converged toward the past on the time axis,
wherein in the three-dimensional display mode, the processor is able to display a summary window for displaying a summary of data content of the plurality of pieces of time series data at a designated point in time on the time axis,
wherein the summary window is provided in the form of a two-dimensional plane developed in a direction orthogonal to the time axis at an arbitrary point in time designated on the time axis.

* * * * *